(12) United States Patent
Raskin et al.

(10) Patent No.: US 10,441,594 B2
(45) Date of Patent: Oct. 15, 2019

(54) METHODS OF MAKING QUINOA LEACHATES AND USES THEREOF

(71) Applicant: RUTGERS, THE STATE UNIVERSITY OF NEW JERSEY, New Brunswick, NJ (US)

(72) Inventors: Ilya Raskin, Manalapan, NJ (US); Brittany Graf, Pine Brook, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 422 days.

(21) Appl. No.: 14/562,238

(22) Filed: Dec. 5, 2014

(65) Prior Publication Data

US 2015/0157644 A1 Jun. 11, 2015

Related U.S. Application Data

(60) Provisional application No. 61/912,843, filed on Dec. 6, 2013.

(51) Int. Cl.
  *A61K 36/00* (2006.01)
  *A61K 31/575* (2006.01)
  *A61K 36/21* (2006.01)

(52) U.S. Cl.
  CPC .......... *A61K 31/575* (2013.01); *A61K 36/21* (2013.01); *A61K 2236/00* (2013.01)

(58) Field of Classification Search
  CPC .................................................. A61K 36/00
  USPC ........................................................ 424/725
  See application file for complete search history.

(56) References Cited

U.S. PATENT DOCUMENTS

2011/0033561 A1* 2/2011 Veillet .................... A61K 31/56
424/725

FOREIGN PATENT DOCUMENTS

| CN | 101100475 | * | 1/2008 |
| CN | 101647571 | * | 2/2010 |
| CN | 102060829 | * | 10/2012 |
| GB | 001156717 | * | 7/1969 |
| JP | 2000-336024 | * | 5/2000 |

OTHER PUBLICATIONS

Foucault et al., "Quinoa Extract Enriched in 20-Hydroxyecdysone Protects Mice from diet-induced obesity and modulates adipokines expression", Obesity, vol. 20, issue 2, pp. 1-19, published Sep. 6, 2012.*
Abugoch James, Quinoa (*Chenopodium quinoa* Willd.): Composition, Chemistry, Nutritional, and Functional Properties, *Adv. Food. Nut. Res.*, 58:1-31 (2009).
Arnault et al., Dietary effects of phytoecdysones in the leek-moth, Acrolepiopsis assectella Zell. (Lepidoptera: Acrolepiidae), *J Chem Ecol*, 12(10): 1979-86 (1986).
Bakrim et al., Ecdysteroids in spinach (Spinacia oleracea L.): biosynthesis, transport and regulation of levels, *Plant Physiol Biochem*, 46(10): 844-54 (2008).
Báthori, Phytoecdysteroids effects on mammalians, isolation and analysis, *Mini Rev Med Chem*, 2(3): 285-293 (2002).
Cheng et al., In vivo and in vitro antidiabetic effects of aqueous cinnamon extract and cinnamon polyphenol-enhanced food matrix, *Food Chem*, 135(4): 2994-3002, (2012).
da-Silva et al., The small polyphenolic molecule kaempferol increases cellular energy expenditure and thyroid hormone activation, *Diabetes*, 56(3): 767-76 (2007).
Dinan et al., Taxonomic disribution of phytoecdysteroids in seeds of members of the chenopodiaceae, *Biochem Syst Ecol*, 26(5):553-76 (1998).
Dinan et al., The effects of ingested 20-hydroxyecdysone on the larvae of Aglais urticae, Inachis io, Cynthia cardui (Lepidoptera, Nymphalidae) and Tyria jacobaeae (Lepidoptera, Arctiidae), *J Insect Physiol*, 43(4): 315-327 (1997).
Dinan, L., The Karlson Lecture. Phytoecdysteroids: what use are they?, *Arch Insect Biochem Physiol*, 72(3): 126-141(2009).
Fao, Master plan for the international year of quinoa: a future sown thousands of years ago. pp. 1-26 (2012).
Fao, Quinoa: an ancient crop to contribute to world food security, 1-55 (2011).
Foucault et al., Quinoa extract enriched in 20-hydroxyecdysone protects mice from diet-induced obesity and modulates adipokines expression, *Obesity*, 20(2): 270-77 (2011).
Gorelick-Feldman et al., Phytoecdysteroids increase protein synthesis in skeletal muscle cells, *J Agric Food Chem*, 56(10): 3532-37 (2008).
Grace et al., Hypoglycemic activity of a novel anthocyanin-rich formulation from lowbush blueberry, *Vaccinium angustifolium* Aiton, *Phytomedicine*, 16(5): 406-15 (2009).
Graf et al., Innovations in Health Value and Functional Food Development of Quinoa (*Chenopodium quinoa* Willd)., *Compr. Rev. Food. Sci. Food. Saf.*, 14(4):431-45 (2015).
Graf et al., Plant-derived therapeutics for the treatment of metabolic syndrome, *Curr Opin Investig Drugs*, 11(10): 1107-15 (2010).
Graf et al., Quinoa seeds leach phytoecdysteroids and other compounds with anti-diabetic properties, *Food Chem.*, 163:178-85 (2014).
Jeong et al., Quercetin ameliorates hyperglycemia and dyslipidemia and improves antioxidant status in type 2 diabetic db/db mice, *Nutr Res Pract*, 6(3): 201-7 (2012).
Kapur et al., Beneficial effects of beta-edysone on the joint, epiphyseal cartilage tissue and trabecular bone in ovariectomized rats, *Phytomedicine*, 17(5): 350-5 (2010).
Kellogg et al., Alaskan wild berry resources and human health under the cloud of climate change, *J Agric Food Chem*, 58(7): 3884-3900 (2010).
Kelly, Quercetin: monograph, *Altern Med Rev*, 16(2): 172-194 (2011).
Kizelsztein et al., 20-Hydroxyecdysone decreases weight and hyperglycemia in a diet-induced obesity mice model, *Am J Physiol Endocrinol Metab*, 296(3): E433-3 (2009).

(Continued)

Primary Examiner — Michael V Meller
(74) *Attorney, Agent, or Firm* — Marshall, Gerstein & Borun LLP

(57) ABSTRACT

The present application is directed to materials and method for producing leachates from a plant of the Amaranthaceae family.

8 Claims, 6 Drawing Sheets

(56) References Cited

OTHER PUBLICATIONS

Kokoska et al., Chemistry and pharmacology of Rhaponticum carthamoides: a review, *Phytochemistry*, 70(7): 842-855 (2009).

Kuljanabhagavad et al., Biological activities and chemistry of saponins from Chenopodium quinoa Willd, *Phytochem Rev*, 8(2): 473-490 (2009).

Kumpun et al., Ecdysteroids from Chenopodium quinoa Willd., an ancient Andean crop of high nutritional value, *Food Chem*, 125(4): 1226-34 (2011).

Lafont et al., Practical uses of ecdysteroids in mammals including humans: an update, J. Insect. Sci., 3(7):1-30 (2003).

Lafont, Phytoecdysteroids in world flora: diversity, distribution, biosynthesis and evolution, *Russ J Plant Physiol*, 45(3): 276-295 (1998).

Le, A., Quinoa (Chenopodium quinoa Willd.): composition, chemistry, nutritional and functional properties, *Adv Food Nutr Res.* 58(1): 1-31 (2009).

Marion-Poll et al., Taste detection of phytoecdysteroids in larvae of Bombyx mori, Spodoptera littoralis and Ostrinia nubilalis, *J Insect Physiol*, 48(4): 467-476 (2002).

Nahar et al., Cheoalbuside: an antioxidant phenolic glycoside from the seeds of Che3nopodium album L. (Chenopodiaceae), *Brazil. J. Pharmaco.*, 15(4):279-82 (2005).

O'Day et al. Corn Insect Pests: A Diagnostic Guide, Missouri Manual 166, Illinois Manual C1358, Columbia, Missouri: MU Extension, University of Missouri, 49 p., (1998).

Pavela et al., Systemic effects of phytoecdysteroids on the cabbage aphid *brevicoryne brassicae* (Sternorrhyncha: Aphididae), *Eur. J. Entomol.*, 102:347-53 (2005).

Rharrabe et al., Dietary effects of four phytoecdysteroids on growth and development of the Indian meal moth, Plodia interpunctella, *J. Insect. Sci.*, 10(13): 1-12 (2010).

Ribnicky et al., Improved absorption and bioactivity of active compounds from an anti-diabetic extract of Artemisia dracunculus L, *Int J Pharm*, 370(1-2): 87-92 (2009).

Rojo et al., In vitro and in vivo anti-diabetic effects of anthocyanins from maqui berry (Aristotelia chilensis), *Food Chem.*, 131(2): 387-396 (2012).

Roopchand et al., Biochemical analysis and in vivo hypoglycemic activity of a grape polyphenol-soybean flour complex, *J Agric Food Chem.*, 60(36): 8860-8865 (2012).

Roopchand et al., Efficient sorption of polyphenols to soybean flour enables natural fortification of foods, *Food Chem*, 131(4): 1193-200 (2012).

Saragusti et al., Inhibitory effect of quercetin on matrix metalloproteinase 9 activity molecular mechanism and structure-activity relationship of the flavonoid-enzyme intereaction, *Eur J Dermatol*, 644(1-3): 138-145 (2010).

Seidlova-Wuttke et al., Beta-ecdysone has bone protective but no estrogenic effects in ovariectomized rats, *Phytomedicine*, 17(11): 884-9 (2010).

Selvaraj et al., Molecular Docking Studies of Rutin on Matrix Metalloproteinase, *Insights Biomed.*, 1(1-4): (2016).

Shi et al., Saponins from edible legumes: chemistry, processing, and health benefits, J. Med. Food, 7(1): 67-78 (2004).

Singh et al., The dietary effects of 20-hydroxyecdysone on the development of housefly, *J. Insect. Physiol*, 26(2): 139-42 (1980).

Slama et al., Insect hormones—ecdysteroids: their presence and actions in vertebrates, *Eur J Entomo*, 92(1): 355-377 (1995).

Vega-Galvez et al., Nutrition facts and functional potential of quinoa (Chenopodium quinoa Willd.). an ancient Andean grain: a review, *J. Sci. Food Agric.*, 90(15): 2541-2547 (2010).

Zhang et al., Increasing dietary leucine intake reduces diet-induced obesity and improves glucose and cholesterol metabolism in mice via multimechanisms, Diabetes, 56(6): 1647-1654 (2007).

Zhu et al., Ecdysteroids of quinoa seeds (Chenopodium quinoa Willd.), *J. Agric. Food Chem.*, 49(5): 2576-2578 (2001).

\* cited by examiner ns and Uses Thereof

METHODS OF MAKING QUINOA LEACHATES AND USES THEREOF

FIELD

The disclosed subject matter relates generally to the field of bioactive compounds extracted from plant materials and methods of obtaining and using such compounds.

BACKGROUND

Quinoa (*Chenopodium quinoa* Willd.), a nutritious and stress tolerant crop of the Amaranthaceae family, is rapidly gaining popularity as a functional food and nutraceutical (1). *Quinoa*'s long history of use as a subsistence crop and wellness-promoting agent began 5,000-7,000 years ago as the "mother grain" of the ancient Incas. It was consumed for endurance properties by the Incan army, served to children and elders to promote growth and wellness, used to treat fractures and wounds, and incorporated in many medicinal formulations (2,3). Today the crop remains an important endurance-enhancing food source for rural indigenous people in South America and has found its way to kitchens throughout the world (1,4). Though *quinoa* is primarily grown in the Bolivian Altiplano, the crop is widely cultivated in South America (Columbia, Ecuador, Peru, Chile, and Argentina), as well as Europe, Asia, Africa, and North America.

Among agricultural food crops that have been regularly sold and consumed in the United States, *quinoa* is known to be a rich source of phytoecdysteroids (6,7). Phytoecdysteroids are polyhydroxylated steroids structurally related to insect molting hormones. The most prevalent phytoecdysteroid, 20-hydroxyecdysone (20-HE), has been extensively investigated for its insect defense properties (8). 20-HE, also known as ecdysterone or beta-ecdysone, has been shown to deter insect herbivory, delay development, and cause lethality to insect larvae (9-13).

Phytoecdysteroids have a wide range of therapeutic effects in mammals (8), including anabolic, performance enhancing (14, 15), anti-osteoporotic (16, 17) and wound healing properties (18). These molecules are considered the primary bioactive components of the traditional Chinese and Siberian herbs *Ajuga turkestanica, Rhaponticum carthamoides*, and *Cyanotis vaga* (15, 19, 20). Phytoecdysteroids, extracted from these botanical sources, have been marketed and sold in commercially available health products as adaptogens, body building agents, stress reducers, performance enhancers, and cosmetics (21).

Recent studies have demonstrated the role of 20-HE administration in metabolic syndrome (22, 23). Metabolic syndrome is a cluster of coexisting disorders including hyperglycemia/insulin resistance, excess abdominal fat, hypertension and dyslipidemia. Improvement in these metabolic conditions can greatly reduce an individual's likelihood of developing type 2 diabetes, cardiovascular disease, and stroke (24). Chronic administration of 20-HE (10 mg/kg body weight for 13 wk) to diet-induced obese, hyperglycemic mice significantly lowered blood glucose levels, increased insulin sensitivity, decreased body weight, and reduced adiposity 41% compared with control without affecting food consumption (22). Furthermore, a *quinoa* seed extract enriched to 1.9% 20-HE induced anti-diabetic and anti-obesity effects similar to administration of 20-HE alone (6 mg/kg body weight for 3 wk) in diet-induced obese, hyperglycemic mice (23).

SUMMARY

The present disclosure is based on the discovery that the phytoecdysteroid 20-hydroxyecdysone (20-HE) can be obtained (e.g., leached or actively secreted) from germinating *quinoa* seed material in a simple one-step process that does not destroy the integrity of the seed material (e.g., intact seeds or seeds lacking the outer layer). In one aspect, described herein is a method of producing a leachate from a plant of the Amaranthaceae family comprising contacting a seed from a plant of the Amaranthaceae family with a leaching fluid to produce a leaching mixture; and separating the seed from the leaching mixture, thereby producing a leachate from the plant of the Amaranthaceae family. In some embodiments, the plant is a *Chenopodium quinoa* plant. In some embodiments, the seed is an intact seed or a seed lacking the outer layer. In some embodiments, the leaching fluid is selected from the group consisting of water, n-butanol, isopropanol, n-propanol, ethanol, methanol, heptane, hexane, pentane, ethylacetate, acetone, methylene chloride, acetic acid, citric acid, nitromethane and formic acid. In some embodiments, the leaching fluid comprises 60-80% ethanol.

The separating step can be performed using any method known in the art including, but not limited to, filtration, sedimentation, centrifugation, speed vacuum, evaporation, including reduced-pressure evaporation (e.g., rotoevaporation or rotavap), reduced-pressure distillation, precipitation, lyophilization and adsorption.

In some embodiments, the contacting step is performed at a temperature of less than 80° C. In some embodiments, the contacting step is performed at room temperature.

Leachates produced by a method disclosed herein are also provided. In some embodiments, the leachate comprises from about 1 µg to about 400 µg 20-hydroxyecdysone (20-HE) per gram of seed. In some embodiments, the leachate comprises at least 0.5 mg 20-hydroxyecdysone (20-HE) per gram of leachate. In some embodiments, the leachate further comprises at least 0.5 mg total polyphenol content per gram of leachate.

In any of the ranges described herein, the endpoints of the range are included in the range. Additional features and variations of the invention will be apparent to those skilled in the art from the entirety of this application and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

DETAILED DESCRIPTION

Figure 1:
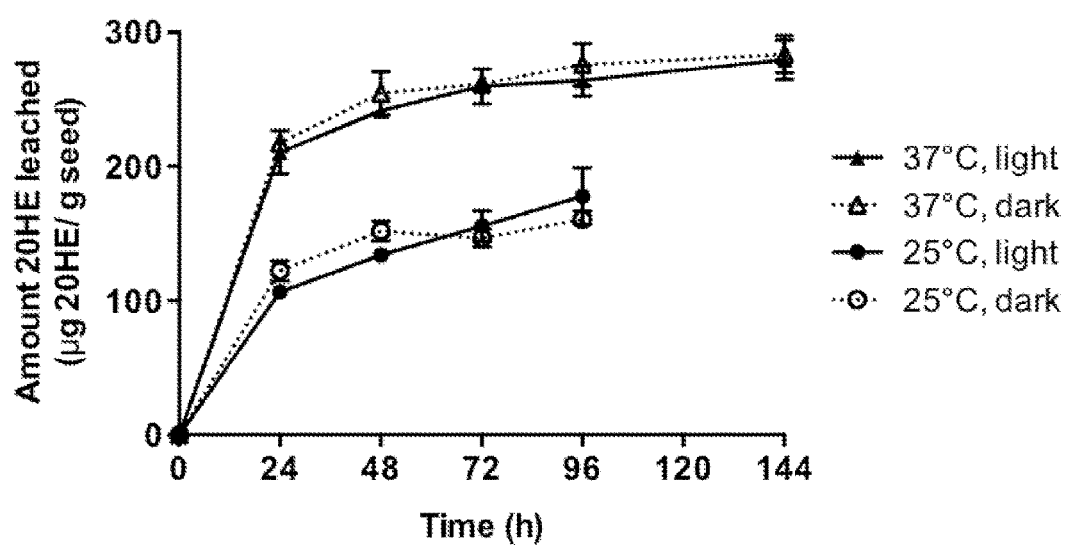
FIG. 1. 20-Hydroxyecdysone (20-HE) leached from *quinoa* seeds into water cumulatively over time. AlterEco Red *quinoa* seeds were surface-sterilized and immersed into sterile water for 24-144 hours under light or dark conditions at 25 or 37° C. 20-HE content was determined in dried leachates by LC-UV-MS. Data are the mean±SEM (n=3).

The disclosure is based on the discovery that the phytoecdysteroid 20-hydroxyecdysone (20-HE) can be obtained, e.g., by leaching or active secretion, from germinating *quinoa* seeds in a simple one-step process that does not destroy the integrity of the seed (e.g., intact seed or seed lacking the outer layer). Conventional 20-HE-enriched *quinoa* extracts are produced in a three-step process that requires boiling and extracting pulverized or ground *quinoa* seeds (23). In contrast, the one-step process disclosed herein preserves the integrity of *quinoa* seed materials, such as intact seeds, which allows for their use as food after the leaching process has been performed.

In one aspect, described herein is a method of producing a leachate from a plant seed of the Amaranthaceae family comprising contacting a seed from the plant of the Amaranthaceae family with a leaching fluid to produce a leaching mixture; and separating the seed from the leaching mixture, thereby producing the leachate from the plant seed of the Amaranthaceae family. In some embodiments, the plant of the Amaranthaceae family is a *Chenopodium quinoa* plant. In some embodiments, the seed material is an intact seed.

The methods described herein utilize a seed, e.g., an intact seed, of a plant from the Amaranthaceae family (e.g., a *Chenopodium quinoa* plant). The term "intact seed" as used herein refers to a seed from a plant of the Amaranthaceae family that has not been ground, pulverized, blended, or otherwise mechanically altered such that the integrity of the seed is destroyed. In some embodiments, the outer layer i.e. of the *quinoa* seed, which contains bitter-tasting saponins, is removed prior to use in the leaching methods disclosed herein.

Seed materials (e.g., intact seeds) can be separated from the leaching mixture by any method known in the art including, but not limited to, filtration, sedimentation, centrifugation, speed vacuum, evaporation, including reduced-pressure evaporation (e.g., rotoevaporation or rotavap), reduced-pressure distillation, precipitation, lyophilization and adsorption. In some embodiments, the separating step comprises filtering the leaching mixture to produce the leachate. Any filter material and apparatus known in the art are contemplated for use in filtering the leaching mixture.

The phrase "leachate from a plant of the Amaranthaceae family" as used herein means a substance or composition obtained from a seed material (e.g., an intact seed) of a plant of the Amaranthaceae family through the use of a leaching fluid. The term "leaching fluid" as used herein refers to a composition capable of removing or drawing out compound(s) from a substance by the action of the composition passing through the substance. Leaching fluids for use in the methods disclosed herein include, but are not limited to, water, alcohols (e.g., C1 to C10 alcohols such as, ethanol, methanol, n-butanol, n-propanol and isopropanol), alkanes (e.g., C1 to C10), halocarbons, ethers, aromatic solvents, ketones, aqueous solvents, esters, aldehydes and ketones e.g. In some embodiments, ethanol (e.g., 60-80%) is used to practice a leaching method described herein. In some embodiments, the leaching fluid is 70% ethanol. Like water, a benefit of incorporating ethanol in the leaching method is that ethanol is compatible with an ingestible product, and therefore is suitable for incorporation of the leachate into a pill, capsule, tablet, or other ingestible form known in the art.

In some embodiments, the seed material (e.g., intact seed) of the plant are contacted with a volume of leaching fluid at an exemplary ratio of 1:1 (i.e., gram of seed material to volume of leaching fluid (mL). In other embodiments, seed material of the plant are contacted with a volume of leaching fluid at an exemplary ratio 1:2, or 1:3, or 1:4, or 1:5, or 1:6, or 1:7, or 1:8, or 1:9 or 1:10. In some embodiments, the seed materials of the plant are contacted with a volume of leaching fluid at a ratio of 1:5.

The contacting step is optionally performed at a temperature of less than 100° C. In some embodiments, the contacting step is performed at a temperature of less than 90° C., or less than 85° C., or less than 80° C., or less than 75° C., or less than 70° C., or less than 65° C., or less than 60° C., or less than 55° C., or less than 50° C., or less than 45° C., or less than 40° C., or less than 35° C., or less than 30° C., or less than 25° C., or less than 20° C. In some embodiments, the contacting step is performed at a temperature of about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., or about 99° C. In some embodiments, the contacting step is performed at room temperature. The term "room temperature" as used herein refers to a temperature generally ranging from 18° C. to 25° C. In some embodiments, the resulting leachate is optionally dried. Exemplary methods of drying the leachate include, but are not limited to, air drying, spray drying, speed vacuum, rotoevaporation (rotovap) and lyophilization.

In some embodiments, the resulting leachate is optionally purified (e.g., by chromatography or other method known in the art) prior to the optional drying step. In some embodiments, the resulting leachate is optionally purified after the drying step.

In some embodiments, a leachate produced by a leaching method disclosed herein comprises at least 1 µg 20-hydroxyecdysone (20-HE) per gram of seed material used in the leaching method. In some embodiments, the leachate comprises at least 1 µg, or at least 5 µg, or at least 10 µg, or at least 15 µg, or at least 20 µg, or at least 25 µg, or at least 30 µg, or at least 35 µg, or at least 40 µg, or at least 45 µg, or at least 50 µg, or at least 60 µg, or at least 70 µg, or at least 80 µg, or at least 90 µg, or at least 95 µg, or at least 100 µg, or at least 125 µg, or at least 150 µg, or at least 200 µg, or at least 250 µg, or at least 300 µg, or at least 350 µg, or at least 400 µg, at least 500 µg, at least 600 µg, at least 700 µg, at least 800 µg or more 20-HE per gram of seed material used in the leaching method. In some embodiments, the leachate comprises about 100-400 µg 20-HE per gram of seed material used in the leaching method.

In some embodiments, a leachate produced by a leaching method disclosed herein comprises at least 0.5 mg 20-HE per gram of the dried leachate. In some embodiments, the leachate comprises at least 0.5 mg, or at least 1 mg, or at least 1.5 mg, or at least 2 mg, or at least 2.5 mg, or at least 3 mg, or at least 3.5 mg, or at least 4 mg, or at least 4.5 mg or at least 5 mg or more 20-HE per gram of dried leachate.

In addition to 20-HE, leachates obtained from plants of the Amaranthaceae family contain other beneficial phytochemicals, such as flavonoids, glycosides, saponins and phytoecdysteroids other than 20-HE. Exemplary phytochemicals present in a leachate produced by a method disclosed herein include, but are not limited to, triterpenoid derivative I, triterpenoid derivative II, quercetin trisaccharide I, quercetin trisaccharide II, quercetin trisaccharide III, kaempferol trisaccharide, quercetin glucoronide, makisterone A, makisterone C, 24-epi-makisterone A, dehydromakisterone A, and ecdysteroid. In some embodiments, a leachate produced by the methods described herein comprises (in addition to a high concentration of 20-HE) at least 1% total polyphenol content per gram of dried leachate. In some embodiments, a leachate produced by the methods described herein comprises at least 1%, or at least 2%, or at least 3%, or at least 4%, or at least 5%, or at least 6%, or at least 7%, or at least 8%, or at least 9%, or at least 10%, or at least 11%, or at least 12%, or at least 13%, or at least 14%, or at least 15%, or at least 16%, or at least 17%, or at least 18%, or at least 19%, or at least 20%, or at least 21%, or at least 22%, or at least 23%, or at least 24%, or at least 25%, or at least 30%, or at least 35% or more total polyphenol content per gram of dried leachate. In some embodiments, an extract produced by the methods described herein comprises a total polyphenol content ranging from 2-5%, or 1-3%, or 2-4%, or 1-5%, or 3-5%, or 3-7% or 4-8% or 5-10%, or 10-15%, or 15-20%, or 20-25%, or 20-30% or 25-30% or more In some embodiments, a leachate produced by a leaching method disclosed herein comprises at least 0.5 mg 20-HE per gram of the dried leachate.

In some embodiments, the leachate comprises at least 0.5 mg, or at least 1 mg, or at least 1.5 mg, or at least 2 mg, or at least 2.5 mg, or at least 3 mg, or at least 3.5 mg, or at least 4 mg, or at least 4.5 mg or at least 5 mg or more total polyphenol content per gram of dried leachate.

In some embodiments, a leachate produced by the methods described herein (or the seed materials separated from the leaching mixture) is incorporated into a consumer product. A consumer product is a product available for purchase and/or use by an individual consumer and includes food products (including, but not limited to, enriched food products (see below), dietary supplements (see below) and medical foods (see below)), cosmetic products and other personal care products.

In some embodiments, a leachate produced by the methods described herein is incorporated into a food product to produce an enriched food product. The term "food product" as used herein refers to any substance containing nutrients that can be ingested by an organism to produce energy, promote health and wellness, stimulate growth, and maintain life. In some embodiments, a leachate produced by the methods described herein is used in the preparation of enriched food products comprising high amounts of 20-HE. The term "enriched food product" as used herein refers to a food product that has been modified to include the leachate produced by the methods disclosed herein, which provides a benefit such as a health/wellness-promoting and/or disease-preventing/mitigating/treating property beyond the basic function of supplying nutrients.

The leachate produced by the methods described herein can be incorporated into any food product. Exemplary food products include, but are not limited to, baked goods (cakes, cookies, crackers, breads, scones and muffins), dairy-type products (including, but not limited to, cheese, yogurt, custards, rice pudding, mousses, ice cream, frozen yogurt, frozen custard), desserts (including, but not limited to, sherbet, sorbet, water-ices, granitas and frozen fruit purees), spreads/margarines, pasta products and other cereal products, meal replacement products, nutrition bars, trail mix, granola, beverages (including, but not limited to, smoothies, water or dairy beverages, and soy-based beverages), and breakfast-type cereal products such as oatmeal. For beverages, the leachate (or 20-HE isolated from the leachate) may be in solution, suspended, emulsified or present as a solid.

In one embodiment, the enriched food product is a meal replacement product. The term "meal replacement product" as used herein refers to an enriched food product that is intended to be eaten in place of a normal meal. Nutrition bars and beverages that are intended to constitute a meal replacement are types of meal replacement products. The term also includes products which are eaten as part of a meal replacement weight loss or weight control plan, for example snack products which are not intended to replace a whole meal by themselves, but which may be used with other such products to replace a meal or which are otherwise intended to be used in the plan. These latter products typically have a calorie content in the range of from 50-200 kilocalories per serving.

In another embodiment, the food product is a dietary supplement. The term "dietary supplement" as used herein refers to a substance taken by mouth that contains a "dietary ingredient" intended to supplement the diet. The term "dietary ingredient" includes, but is not limited to, 20-HE as disclosed herein, as well as vitamins, minerals, herbs or other botanicals, amino acids, and substances such as enzymes, organ tissues, glandulars, and metabolites.

In yet another embodiment, the food product is a medical food. The term "medical food" as used herein means a food which is formulated to be consumed or administered entirely under the supervision of a physician and which is intended for the specific dietary management of a disease or condition for which distinctive nutritional requirements, based on recognized scientific principles, are established by medical evaluation.

In some embodiments, the leachate produced by the methods described herein (or 20-HE isolated from the leachate) are useful as cosmeceuticals. The term "cosmeceutical" as used herein means an ingredient for a cosmetic, body care or hair care personal product having a positive effect on the physical condition of the body (e.g., the skin, the nails, or hair).

Compositions suitable for personal care products generally are formulated as, e.g., shampoos, conditioners, shower gels, liquid hand cleansers, facial cleansers, moisturizers, lotions, skin lotions and creams (such as eye creams and lip creams), facial skin cosmetics (such as blusher and highlighter), eye cosmetics (such as eye shadow, eye brow color, and eye liner), lip cosmetics (such as lip rouge), foundation, concealer, wrinkle-smoothing serums or creams, mascaras, skin facial masks, sunscreens, scalp hair-styling aids, facial hair-styling aids, emulsions, oils, mousses, ointments, milks, pomades, solutions, sprays, aerosols, powders, foams, gels (such as skin gels, eye gels, and lip gels), or other skin or hair products known in the art.

The disclosure contemplates compositions comprising a leachate produced by the methods described herein (or 20-HE obtained from the leachate) that are, in some embodiments, tabletted, encapsulated or otherwise formulated for oral administration. The compositions may be provided as pharmaceutical compositions, nutraceutical compositions (e.g., a dietary supplement), or as a food or beverage additive, as defined by the U.S. Food and Drug Administration. The dosage form for the above compositions is not particularly restricted. For example, liquid solutions, suspensions, emulsions, tablets, pills, capsules, sustained-release formulations, powders, suppositories, liposomes, microparticles, microcapsules, sterile isotonic aqueous buffer solutions, and the like are all contemplated as suitable dosage forms.

The compositions typically include one or more suitable diluents, fillers, salts, disintegrants, binders, lubricants, glidants, wetting agents, controlled release matrices, colorings, flavoring, carriers, excipients, buffers, stabilizers, solubilizers, commercial adjuvants, and/or other additives known in the art.

Any pharmaceutically acceptable (i.e., sterile and acceptably non-toxic as known in the art) liquid, semisolid, or solid diluent that serves as a pharmaceutical vehicle, excipient, or medium can be used. Exemplary diluents include, but are not limited to, polyoxyethylene sorbitan monolaurate, magnesium stearate, calcium phosphate, mineral oil, cocoa butter, and oil of theobroma, methyl- and propylhydroxybenzoate, talc, alginates, carbohydrates, especially mannitol, α-lactose, anhydrous lactose, cellulose, sucrose, dextrose, sorbitol, modified dextrans, gum acacia, and starch. Such compositions may influence the physical state, stability, rate of in vivo release, and rate of in vivo clearance of the functional compounds that are compatible with the disclosed methods and leachates comprising 20-HE.

Pharmaceutically acceptable fillers can include, for example, lactose, microcrystalline cellulose, dicalcium phosphate, tricalcium phosphate, calcium sulfate, dextrose, mannitol, and/or sucrose. Salts, including calcium triphosphate, magnesium carbonate, and sodium chloride, may also be used as fillers in the pharmaceutical compositions.

Binders may be used to hold together the composition containing the enriched substance to form a hard tablet. Exemplary binders include materials from organic products such as acacia, tragacanth, starch and gelatin. Other suitable binders include methyl cellulose (MC), ethyl cellulose (EC) and carboxymethyl cellulose (CMC).

In some embodiments, the composition further comprises a bioavailability enhancer, which acts to increase the absorption of the 20-HE by the body. Bioavailability enhancers can be natural or synthetic compounds. In one embodiment, the enriched food product comprising the enriched solid further comprises one or more bioavailability enhancers in order to enhance the bioavailability of the bioactive natural product(s).

Natural bioavailability enhancers include ginger, a caraway extract, a pepper extract and chitosan. The active compounds in ginger include 6-gingerol and/or 6-shogoal. Caraway oil can also be used as a bioavailability enhancer (U.S. Patent Application Publication No. 2003/022838). Piperine is a compound derived from pepper (*Piper nigrum* or *Piper longum*) that acts as a bioavailability enhancer (U.S. Pat. No. 5,744,161). Piperine is available commercially under the brand name Bioperine® (Sabinsa Corp., Piscataway, N.J.). In some embodiments, the natural bioavailability enhancers is present in an amount of from about 0.02% to about 0.6% by weight based on the total weight of enriched food product.

Examples of suitable synthetic bioavailability enhancers include, but are not limited to, Gelucire®, Labrafil® and Labrasol®, Lauroglycol®, Pleurol Oleique® (Gattefosse Corp., Paramus, N.J.) and Capmul® (Abitec Corp., Columbus, Ohio).

The amount and administration regimen of the composition is based on various factors relevant to the purpose of administration, for example human or animal age, sex, body weight, hormone levels, or other nutritional need of the human or animal. In some embodiments, the composition is administered to an animal in an amount from about 0.001 mg/kg body weight to about 10 g/kg body weight. In some embodiments, the composition is administered to an animal in an amount of about 0.005 mg/kg body weight. In some embodiments, the composition is administered to an animal in an amount of about 0.01 mg/kg body weight, or about 0.05 mg/kg body weight, or about 0.1 mg/kg body weight, or about 1 mg/kg body weight, or about 10 mg/kg body weight, or about 100 mg/kg body weight, or about 250 mg/kg body weight, or about 500 mg/kg body weight, or about 1 g/kg per body weight, or about 2.5 g/kg body weight, or about 5 g/kg body weight, or about 7.5 g/kg body weight, or about 10 g/kg body weight.

A typical regimen may comprise multiple doses of the composition. In one embodiment, the composition is administered once per day and may be administered to an individual at any time. In some embodiments, the composition is administered concurrently, prior to, or at the consumption of a meal. The composition is administered on any periodic schedule suitable for the desired or needed effect, or on an as-needed basis.

It will be appreciated that the leachate produced by the methods described herein is useful in the fields of human medicine and veterinary medicine to provide high levels of 20-HE to a subject in need thereof. Thus, the subject or individual to be treated may be a mammal, such as a human. In addition to humans, subjects include, for example, farm animals such as cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

EXAMPLES

The following Examples are provided to describe the invention in greater detail, and are intended to illustrate, not to limit, the appended claims. Example 1 provides the materials and methods for the experiments described in Examples 2-3. Example 2 demonstrates that 20-hydroxyecdysone (20-HE) can be leached from germinating *quinoa* seeds. Example 3 provides a biochemical analysis of the *quinoa* leachate (QL).

Example 1—Materials and Methods

Materials.

Bolivian-grown red *quinoa* seed were purchased from AlterEco, Inc. (San Francisco, Calif., USA), containing 11% protein, 10% carbohydrate, and 4% fat (Nutrition Facts, AlterEco Red *Quinoa*). Seeds were polished and washed by the producer to remove the outer layer of bitter saponins before distribution. All chemical reagents were obtained from Sigma (St. Louis, Mo.) unless specified otherwise. All water used in the experiments was purified using a Millipore water purification system with a minimum resistivity of 18.2 MΩ cm (Bedford, Mass.).

Aqueous Leaching of 20-HE.

*Quinoa* seeds were surface-sterilized by 1 minute immersion in 70% ethanol, followed by 12 minutes in 1.5% sodium hypochlorite, and rinsed three times with sterile water. Seeds were dried overnight on sterile filter paper. Seeds (about 0.25 g) were incubated in 1 ml sterile $ddH_2O$ in culture tubes for 24, 48, 72, 96, or 144 hours (three replicates per time point) on a shaker at 160 rpm/min in light and dark conditions at 25° C. or 37° C. At the end of each time point, the leachate from each sample was filtered through a 0.45 μm syringe filter (Corning, Inc., Corning, N.Y., USA) into weighed Eppendorf tubes and dried by speed vacuum followed by lyophilization. Dried leachate weights were recorded and each sample was re-dissolved in water to a concentration of 5 mg/ml for LC-UV-MS injection in 5 μl volumes.

LC-UV-MS Analysis.

Standards of 20-HE (Bosche Scientific, New Brunswick, N.J.), makisterone A (A.G. Scientific, Inc., #M1-1080), and quercetin-3-glucoside were dissolved in 70% ethanol at concentrations of 1, 0.1, 0.05, and 0.01 mg/ml and used for chemical identification and quantification by LC-UV-MS at 247 nm with 1 μl injection volumes. Compounds for which no standards were available were putatively identified using retention time, mass signal ([M+H]+, ([M−H]− and fragment m/z), fragmentation pattern, and molecules reported in the literature. 20-HE analogs (24-epi-makisterone A, 24(28)-dehydromakisterone A, and makisterone C) were calculated as 20-HE equivalents (concentrations of individual molecules were estimated using a standard of 20-HE). Concentrations of quercetin and kaempferol glycosides were calculated as quercetin-3-glucoside equivalents.

Analysis was performed using the Dionex® UltiMate 3000 RSLC ultra-high pressure liquid chromatography system, consisting of a workstation with Dionex's Chromeleon v. 6.8 software package, solvent rack/degasser SRD-3400, pulseless chromatography pump HPG-3400RS, autosampler WPS-3000RS, column compartment TCC-3000RS, and photodiode array detector DAD-3000RS. After the photodiode array detector the eluent flow was guided to a Varian 1200L (Varian Inc., Palo Alto, Calif.) triple quadrupole mass spectrometer with electrospray ionization interface (ESI), operated in either positive (5 kV) or negative (−4.5 kV) ionization mode. Drying gas temperature was 280° C. and nitrogen was the sheath gas. The mass detector was used in scanning mode from 65 to 1500 atomic mass units (amu). Data from the Varian 1200L mass detector was collected, compiled and analyzed using Varian's MS Workstation, v. 6.41, SP2. Substances were separated on a Phenomenex® C8 reverse phase column, size 150×2.0 mm, particle size 3 m, pore size 100 Å. The mobile phase consists of 2 components: Solvent A (0.5% ACS grade acetic acid in $ddH_2O$, pH 3-3.5), and Solvent B (100% ACN). The mobile phase flow was 0.2 ml/min, and a gradient mode was used for all analyses. The initial conditions of the gradient were 93% A and 7% B; the proportion reached 73% A and 27% B over 40 min; solvent B reached 100% in the next 5 minutes and was maintained for 2 minutes; the column was re-equilibrated to initial conditions for 13 min. The total run time was set to 60 minutes.

Optimization of Leaching in Ethanol.

*Quinoa* seeds (1.6 g) were incubated in 8 ml aqueous ethanol at varying concentrations (0-95%) in 15 ml tubes on a shaker at 200 rpm/min in the dark over a range of temperatures (25° C.-80° C.) and time points (1-24 hours). Seeds were leached 24 hours at lower temperatures (25° C. and 50° C.) and up to 8 hours at higher temperatures (50° C. and 80° C.). Using optimal solvent, temperature and time conditions, sonication (20 minutes) and solvent acidification (1% acetic acid) were also tested for their effects on 20-HE leaching. Leachates were filtered through 0.45 μm syringe filters into 8 ml glass vials and dried by speed vacuum followed by lyophilization. Dried leachate weights were determined. Aliquots of each sample were re-dissolved in their corresponding solvent (0-95% ethanol) at a concentration of 5 mg/ml and injected in the LC-UV-MS in 1-5 μl volumes.

Optimal leaching conditions were determined by three factors: (1) amount of 20-HE released from seeds into solution (μg 20-HE/gram seed), (2) 20-HE concentration in final dried leachate (μg 20-HE/mg), and (3) yield, or the amount of leachate obtained per gram of seed (mg/gram seed).

Seed Extraction.

*Quinoa* seeds were pulverized in a coffee grinder (Krups, Inc., USA). Seed powder (1.6 g) was mixed with 8 ml 70% ethanol for 4 hours at 25° C.-80° C., centrifuged at 4,000 rpm for 10 minutes at 4° C., filtered, dried, and analyzed as described above.

Production and Analysis of *Quinoa* Leachate (QL) for Biological Study.

*Quinoa* seeds (1 kg) were rinsed in cold water for 5 minutes and leached in 5 L solvent under optimized conditions (70% ethanol, 80° C., 4 h). Leachate was filtered through Whatman filter paper, dried, and weighed. An aliquot of QL was resuspended in 30% ACN at a concentration of 20 mg/ml, filtered, and injected in the LC-UV-MS in 3 µl volumes for analysis of total phytoecdysteroid and total flavonoid glycoside content using methods described above. A separate aliquot of QL (30 g) was used for proximate nutritional and amino acid profile analysis by Eurofins Nutrition Analysis (De Moines, Iowa) according to standard methods. Carbohydrate content was calculated as 100% minus the sum of other nutritional components (protein, oil, moisture, ash). Remaining QL was used for biological study.

Animal Studies.

An acute hypoglycemic study in diet-induced obese mice was performed as described previously (Cheng et al., *Food Chem* 135: 2994-3002, 2012, incorporated herein by reference). Briefly, five-week-old male C57Bl/6J mice (Jackson Labs), acclimated for 1 week with ad libitum access to chow (Purina, No. 5014) and water, and maintained on a very high-fat diet (VHFD) containing 60% fat-derived calories (D12492; Research Diets) for an additional 15 weeks to induce obesity, insulin resistance, and hyperglycemia. Food intake and body weight were monitored weekly. Following a 4-hour fasting period, fasting blood glucose (FBG) was measured using an AlphaTRAK® handheld glucometer (Abbott Labs, Inc.), and mice were randomly divided into FBG-balanced experimental groups.

*Quinoa* leachate (QL) was formulated in 70% Labrasol® (Gattefossé Corp., Paramus, N.J.). The biological activity of QL was tested using an oral ingestion of 0.25 ml per 50 g body weight of vehicle (70% Labrasol®) or QL (250 and 500 mg/kg) (n=7). Metformin® (300 mg/kg, dissolved in water) was administered as a positive control. FBG was reassessed 4 hours post-treatment. Mean FBG values before and after treatment were calculated for each group and compared using paired t-tests in Microsoft Excel. Additionally, final % FBG (final FBG/initial FBG×100) of each mouse was calculated 4 hours post-treatment. Mean final % FBG values for each treatment group were compared to vehicle by 1-way ANOVA followed by Dunnett's post hoc test using Prism 6.0 (GraphPad Software, San Diego, Calif.). $P<0.05$ was considered significant.

Example 2—20-HE Leaches from Germinating Seeds

20-HE leached from *quinoa* seeds into water gradually over the course of 144 hours, with greater leaching occurring at 37° C. (294.0 µg/gram seed) compared with 25° C. (156.5 µg/gram seed) (FIG. 1). Seedlings germinated under all conditions. Greatest seedling growth occurred in seeds incubated in the dark at 25° C. after 96 hours. Light did not impact the amount of 20-HE that leached from the seed compared with seeds germinated in the dark.

Figure 2:
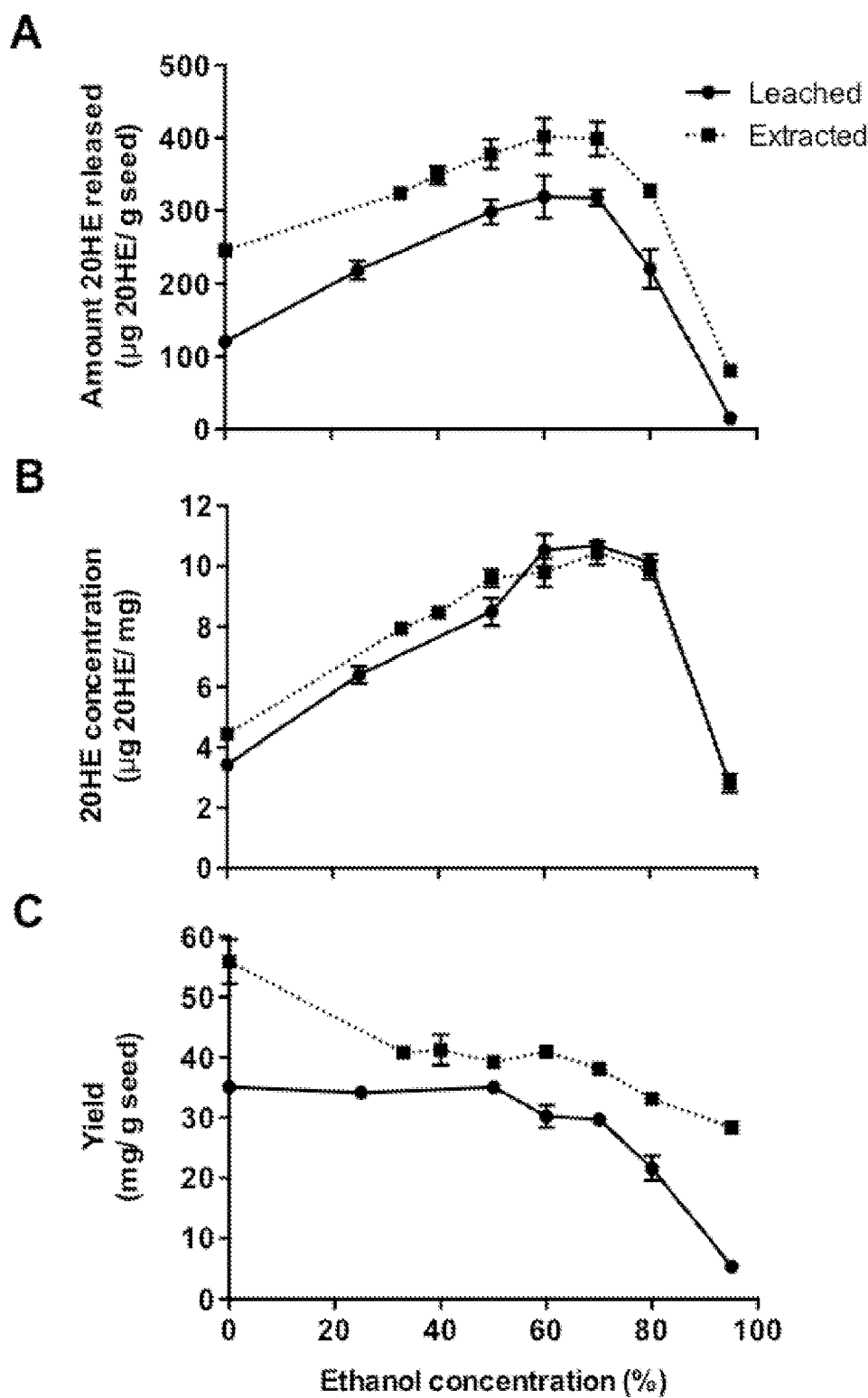
FIG. 2. Leaching versus extraction of 20-hydroxyecdysone (20-HE) from *quinoa* seeds into varying concentrations of ethanol. Intact *quinoa* seeds were incubated in ethanol (0-95%) at 25° C. for 24 hours to produce leachates, or macerated seed material was extracted in ethanol (0-95%) at 25° C. for 4 hours. 20-HE content was determined in dried leachates and extracts by LC-UV-MS. Three parameters were measured, shown from top to bottom: (A) amount of 20-HE released from seeds (μg 20-HE/g seed), (B) 20-HE concentration in the final dried leachate or extract (μg 20-HE/mg dried leachate or extract), and (C) yield of leachate or extract (mg/g seed). Data are the mean±SEM (n=3).

The optimal conditions for leaching 20-HE from *quinoa* seeds was 70% ethanol at 25° C. (FIG. 2A). Extracting ground seeds released 398.8 µg/g seed, whereas leaching intact seeds for 24 hours released 317.8 µg 20-HE/g seed (about 80% as efficient as extraction). Proportionally less seed material was solubilized into 70% ethanol during leaching compared to extraction. Therefore, dried extracts and leachates had similar 20-HE content (10.4 and 10.7 µg 20-HE/g seed, respectively) (FIG. 2B). The optimal ethanol concentration for producing highest 20-HE concentrations in the leachate was between 60% and 80%. The leachate yield, measured as the amount of dried leachate produced from seeds, was generally lower than that of extract produced from ground *quinoa* seeds. For example, leachate yield using 70% ethanol was 29.7 mg/g seed compared to 38.1 mg/g for the extract (FIG. 2C). Amounts of leached 20-HE, its concentration in the leachate and the yield of the leachate decreased dramatically in pure ethanol.

The effects of temperature on the efficiency of 20-HE leaching from intact *quinoa* seeds into 70% ethanol as compared to extraction of ground *quinoa* seeds at the same temperature was then studied. At temperatures above 25° C., more seed material, including 20-HE, was leached into solvent (Table 1).

TABLE 1

Leaching versus extraction of 20-HE from quinoa seeds at various temperatures.

|  | Leached | | | | Extracted | | |
| --- | --- | --- | --- | --- | --- | --- | --- |
| Temperature (° C.) | 25 | 37 | 50 | 80 | 25 | 80 | 80 |
| Time (h) | 24 | 24 | 4 | 4 | 4 | 4 | 4* |
| Amount 20-HE released (µg 20-HE/g seed) | 317.8 (±11.0) | 327.2 (±35.9) | 367.6 (±4.8) | 491.3 (±1.0) | 398.8 (±23.6) | 423.1 (±1.6) | 448.8 (±18.8) |
| 20-HE concentration (µg 20-HE/mg) | 10.7 (±0.2) | 9.2 (±0.9) | 11.4 (±0.2) | 10.9 (±0.1) | 10.4 (±0.4) | 9.3 (±0.4) | 6.2 (±0.2) |
| Yield (mg/g seed) | 29.7 (±0.7) | 35.6 (±0.6) | 32.3 (±0.3) | 45.0 (±0.5) | 38.1 (±0.9) | 45.8 (±1.8) | 72.4 (±1.0) |

Intact quinoa seeds or macerated seed powder were incubated in 70% ethanol (5 ml/g seed) at increasing temperatures (25, 50, 70, or 80° C.) for 4 or 24 h. Leachates and extracts were dried analyzed for 20-HE content by LC-UV. Data are the mean ± SEM (n = 3).
*Macerated seed material was extracted 3 times consecutively.

Figure 3:
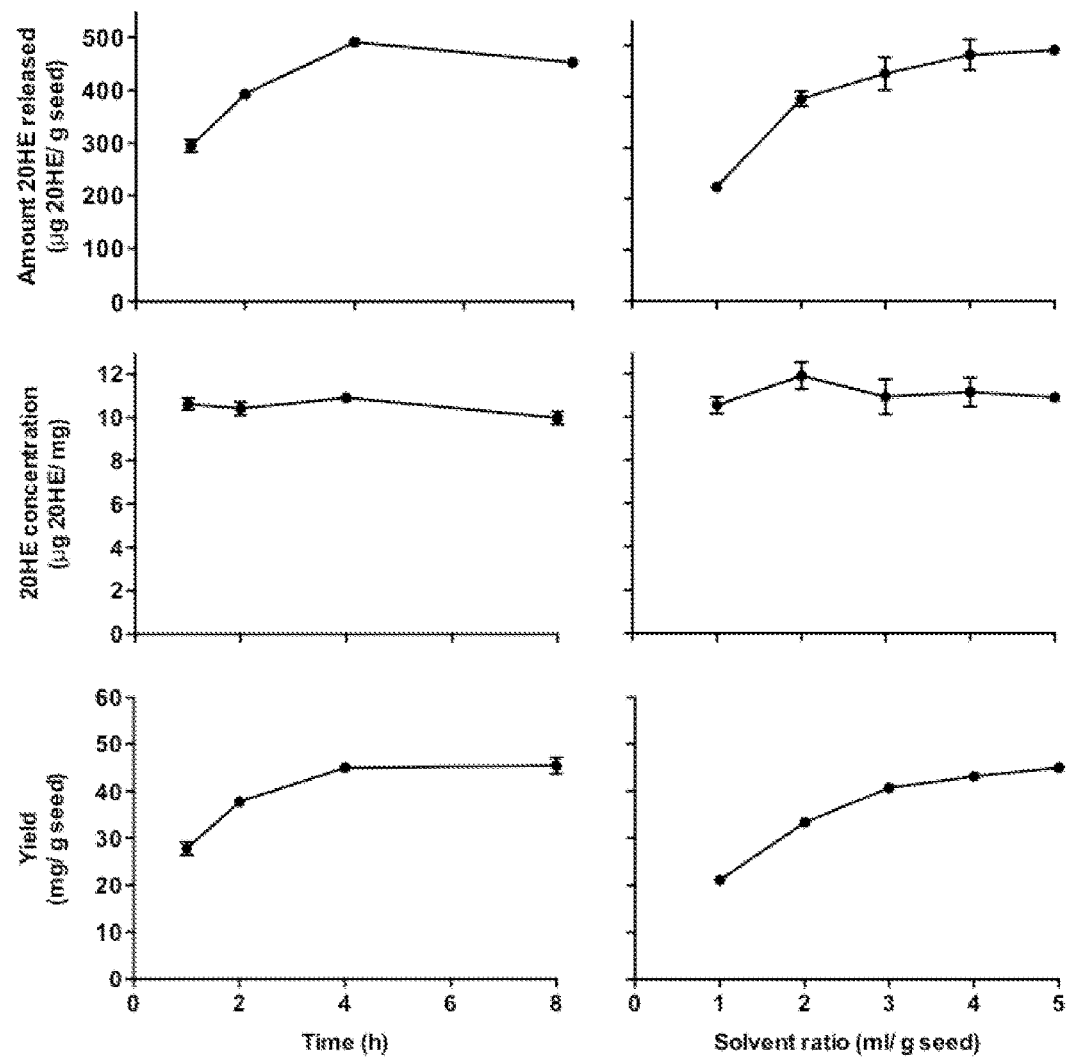
FIG. 3. Effect of time and solvent ratio on leaching of 20-hydroxyecdysone (20-HE) from *quinoa* seeds. Left: Seeds were incubated in 70% ethanol (5 ml/g seed) at 80° C. for increasing time durations (1-8 h). Right: Seeds were incubated in increasing volume ratios of 70% ethanol (1-5 ml/g seed) under optimal time (4 h) and temperature (80° C.). Data are the mean±SEM (n=3).

Compared with total 20-HE that was obtained from repeated extraction of ground seeds, leaching intact seeds in 70% ethanol at 80° C. for 4 hours released the maximum amount of 20-HE available in the seed (491.3 µg/g) (Table 1). Under these conditions, leachate yield was 4.5% and 20-HE content of dried leachate was 1.09%. Leaching was further optimized by time (1-8 hours) and solvent to seed ratio (1-5 ml/gram seed), demonstrating that 4 hours of leaching and 5 ml solvent:g seed solvent:seed ratio produced optimal conditions for leaching most of the 20-HE from seeds (FIG. 3). Sonication and solvent acidification did not affect the amount of 20-HE leached from seeds or the 20-HE concentration in the dried leachate.

Example 3—Biochemical Analysis of *Quinoa* Leachate (QL)

QL was prepared for phytochemical, nutritional, and biological studies from 1 kg seed under optimal conditions, yielding 41.0 g QL. Phytochemical content was determined using LC-UV-MS (Table 2).

TABLE 2

Retention time, putative chemical identification, m/z, and concentration of phytochemicals in quina leachate (QL).

| Peak No. | UV $R_t$ (min) | Compound | $[M + H]^+$ | $[M - H]^-$ | Fragment m/z | Conc. (mg/g) |
|---|---|---|---|---|---|---|
| 1 | 17.97 | Triterpenoid derivative I | | 664* | | — |
| 2 | 18.82 | Triterpenoid derivative II | | 664* | | — |
| 3 | 20.68 | Quercetin trisaccharide I | 757 | 755 | 611, 303 | 4.85 |
| 4 | 21.39 | Quercetin trisaccharide II | 743 | 741 | 611, 465, 303 | 2.98 |
| 5 | 22.06 | Quercetin trisaccharide III | 743 | 741 | 611, 303 | 0.26 |
| 6 | 23.34 | Kaempferol trisaccharide | 741 | 739 | 595, 449, 287 | 2.31 |
| 7 | 24.62 | Triterpenoid derivative III | | 609* | | — |
| 8 | 24.92 | Quercetin glucoronide | 479 | | 303 | 0.27 |
| 9 | 25.26 | 20-Hydroxyecdysone | 481 | 539* | 463 | 8.60 |
| 10 | 29.83 | Makisterone A | 495 | | 477, 459, 441 | 0.46 |
| 11 | 30.23 | 24-Epi-makisterone A | 495 | | 477, 459, 441 | 0.30 |
| 12 | 30.94 | 24(28)-Dehydromakisterone A | 493 | | 475, 457, 439 | 0.45 |
| 13 | 34.18 | Ecdysteroid | 465 | 464 | 447, 429 | 0.12 |
| 14 | 35.19 | Steroid | 427 | | | — |
| 15 | 38.73 | Makisterone C | 509 | | 491 | 0.10 |
| | | Total Phytoecdysteroid | | | | 10.03 |
| | | Total Flavonoid Glycoside | | | | 10.68 |

$R_t$ = retention time
Conc. = concentration
*Indicates the reported $[M - H]^-$ represents an acetic acid adduct $[M - H + C_2H_4O_2]^-$.

Figure 4:
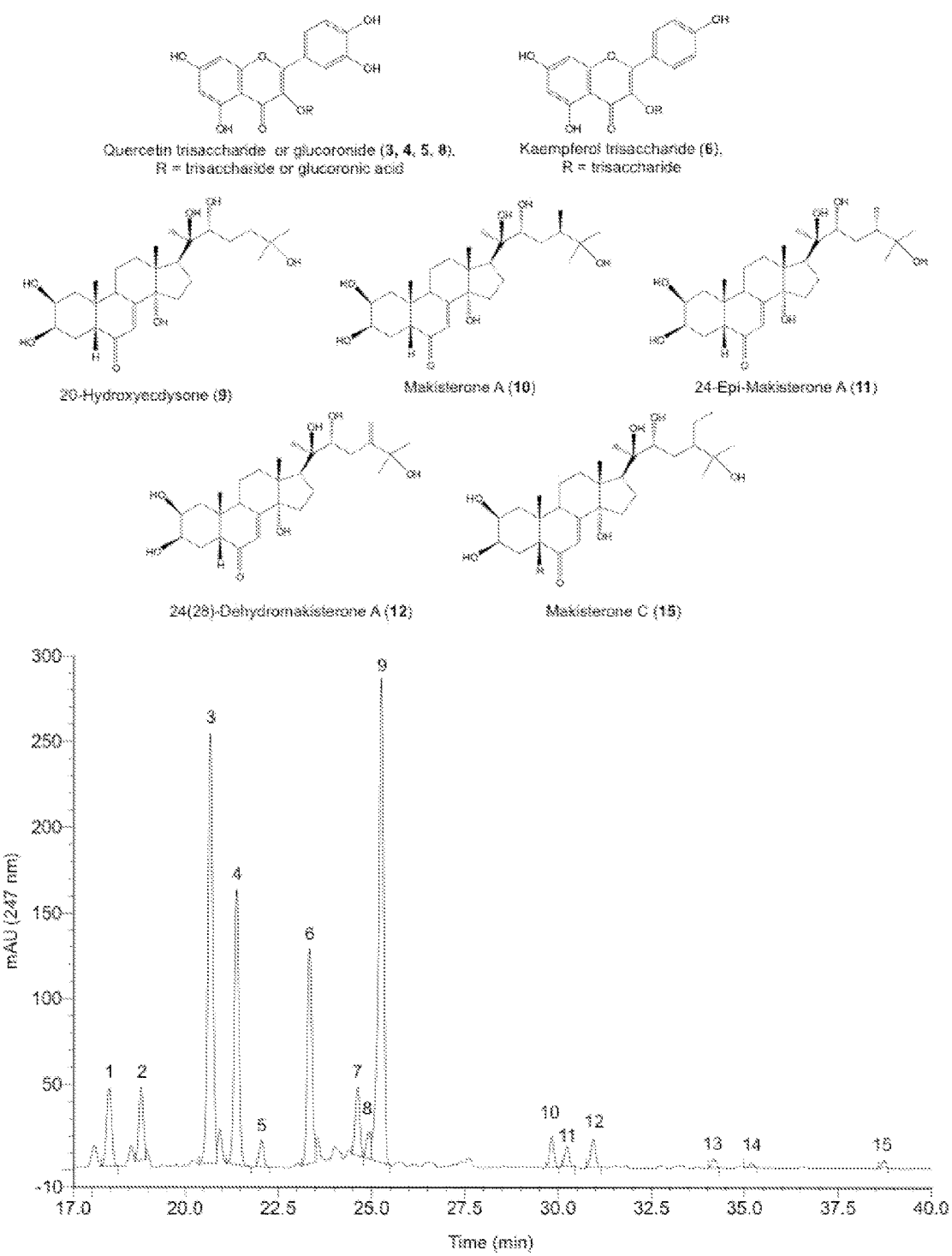
FIG. 4. Molecular structures and LC-UV chromatogram at 247 nm of phytochemicals putatively identified in *Quinoa* leachate (i.e., QL). QL was dissolved in 30% acetonitrile (20 mg/ml) and 3 μl was injected for chemical characterization alongside standards of 20-HE, makisterone A, and quercetin-3-glucoside via LC-UV using a C8 column with a gradient of 7 to 27% acetonitrile over 40 min. Compounds were putatively identified by UV retention time, MS m/z and fragmentation pattern, and based on *quinoa* compounds reported in the literature. Numbers indicate peaks corresponding with the compounds listed in Table 3.

FIG. 4 shows the molecular structures and LC-UV chromatogram at 247 nm of QL phytochemical components. Fifteen peaks corresponding with fifteen different molecules were identified as listed in Table 2, including 4 quercetin glycosides, 1 kaempferol glycoside, and 5 phytoecdysteroids (20-HE, makisterone A, epi-makisterone A, 24(28)-dehydromakisterone A, and makisterone C). 20-HE constituted 0.86% of QL, whereas total phytoecdysteroid content was close to 1%. Quercetin and kaempferol glycosides constituted a total of 1.07% of QL. Other components, determined by proximate nutritional analysis of QL, included protein (20.39%), carbohydrate (53.61%), oil (15.50%), moisture (3.53%), and ash (6.97%). Since carbohydrate content was calculated based on the sum of other nutritional components, actual carbohydrate content may be slightly lower in order to account for the content of secondary metabolites in QL (e.g., phytoecdsyteroids, flavonoid glycosides, saponins). Among total protein content, 0.37% consisted of branched chain amino acids (leucine, isoleucine, and valine) (Table 3).

TABLE 3

Proximate nutritional analysis and amino acid profile of quinoa leachate (QL).

| Nutritional Component | Content (%) |
|---|---|
| Total protein | 20.39 |
| Leucine | 0.08 |
| Isoleucine | 0.08 |
| Valine | 0.21 |
| Threonine | 0.13 |
| Phenylalanine | 0.12 |
| Lysine | 0.20 |
| Histidine | 0.18 |
| Aspartic acid | 0.56 |
| Serine | 0.16 |
| Glutamic acid | 1.45 |
| Proline | 0.29 |
| Glycine | 0.34 |
| Alanine | 0.33 |
| Tyrosine | 0.08 |
| Arginine | 0.29 |
| Carbohydrates | 53.61* |
| Fat | 15.50 |
| Moisture | 3.53 |
| Ash | 6.97 |
| TOTAL | 100.00 |

Analysis was performed by Eurofins Nutrition Analysis (Des Moines, IA). Caloric content of QL is 4.36 kcal/g.
*Carbohydrate content was calculated to total 100.00% following total protein, fat, moisture, and ash analysis. Therefore, the concentration of secondary metabolite in QL (phytoecdysteroids, flavonoid glycosides, saponins) should be subtracted from the carbohydrate content reported here.

Post-leached seeds, representing 95.9% of the initial seed weight retained their shape, form, and color. Post-leached seeds can be roasted and consumed directly, or incorporated in health food bars and snacks. The seeds can also be separated to individual nutritional components (protein, oil, and starch). Therefore, *quinoa* seed leaching may be a way to harness the clinically therapeutic benefits of *quinoa* phytochemicals while preserving the nutritional benefits of non-leached *quinoa* components.

The biochemical characterization provided in this Example corroborates previous reports that *quinoa* seeds contain relatively high levels of phytoecdysteroids. Zhu et al. (2001) were the first to isolate and identify phytoecdysteroids from *quinoa* seeds, reporting 30 µg 20HE/g seed. Kumpun et al. (2011) screened 20HE content from various sources of *quinoa* seeds, finding a range of 184-484 µg 20HE/g *quinoa* seed. 20-HE constituted 61.9% and 88.6% of total phytoecdysteroids isolated from *quinoa* seeds in these studies, respectively. As demonstrated herein, AlterEco red *quinoa* seeds contained 491.3 µg 20-HE/gram seed, constituting 85.7% of total phytoecdysteroids.

In summary, the majority of phytodecsteroids stored within intact *quinoa* seeds can be leached, along with some other biologically active compounds, into the surrounding medium, a leaching fluid. QL production using ethanol leaves behind essentially intact *quinoa* seed material (e.g., intact seeds) that still contain macronutrients (protein, starch and oil) that can be utilized as food.

Example 4—In Vivo Hypoglycemic Effect of *Quinoa* Leachate

Figure 5:
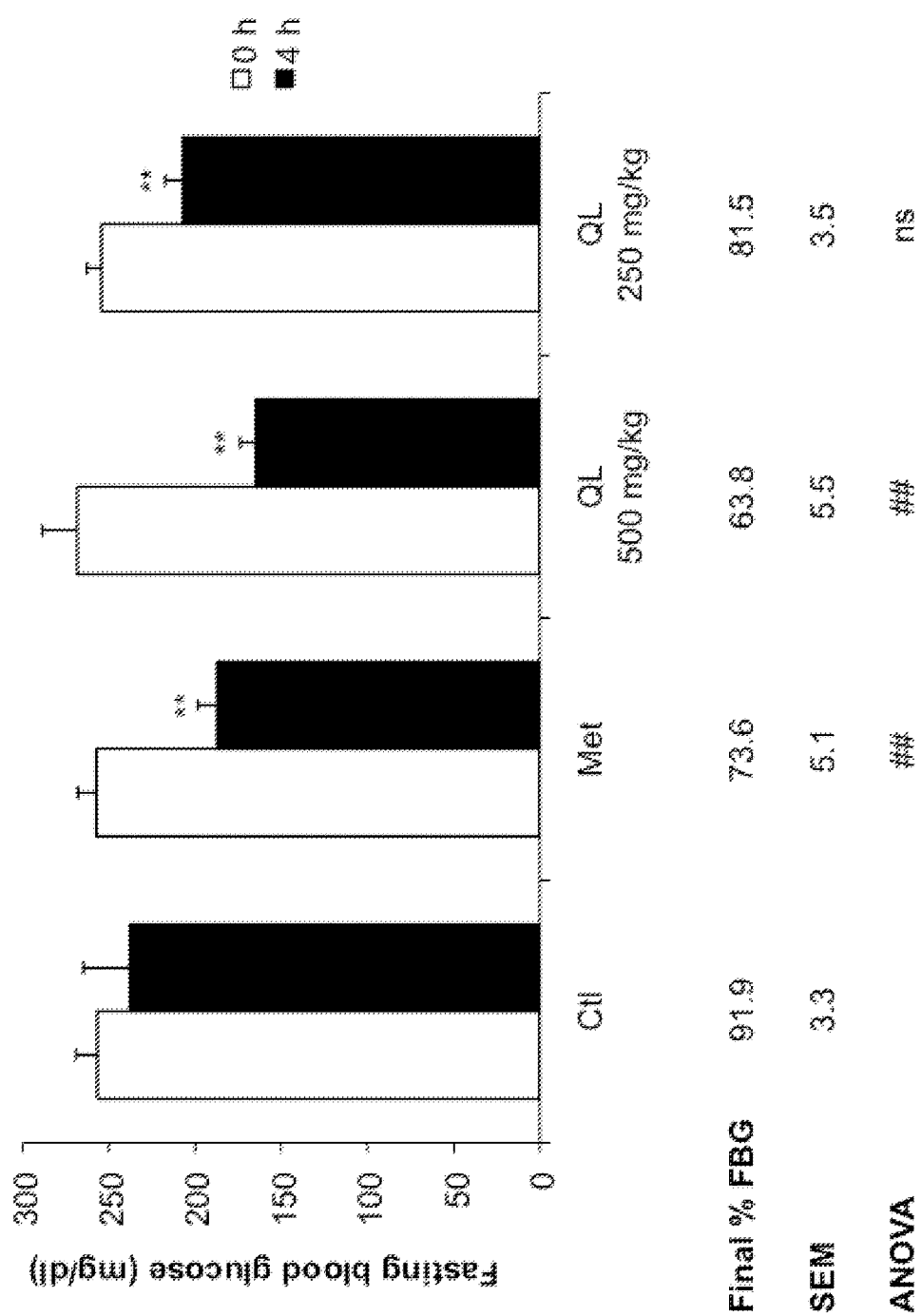
FIG. 5. *Quinoa* leachate (QL) lowers fasting blood glucose (FBG) in obese, hyperglycemic C57BL/6J mice. QL was dissolved in 70% Labrasol (vehicle). FBG was determined via tail-nick before and 4 hours after administration of vehicle (Ctl), 300 mg/kg Metformin® (Met, positive control), or QL (250 and 500 mg/kg). Data are the mean±SEM (n=7). **$P<0.01$ (2-tailed, paired t-test comparing before and after treatment). Values reported below the x-axis are the results of mean final % FBG, SEM, and ANOVA analysis for each group. Final % FBG was calculated for individual mice as post-treatment FBG/pre-treatment FBG×100. ##$P<0.01$ and ns=no significance when compared to control by 1-way ANOVA followed by Dunnett's post hoc test.

Acute oral administration of *quinoa* leachate (QL) demonstrated a dose dependent decrease in fasting blood glucose (FBG) in diet-induced obese, hyperglycemic mice (C57BL/6J) with FBG levels above 200 mg/dl. Metformin (300 mg/kg) and QL (500 and 250 mg/kg) significantly lowered FBG levels 4 hours after oral administration (See FIG. 5). Relative to initial FBG levels of individual mice, 500 and 250 mg/kg QL decreased FBG levels by 36.2% and 18.5%, respectively. Metformin and the higher dose of QL showed significant hypoglycemic effects compared with control by 1-way ANOVA followed by Dunnett's post hoc test.

Example 5—Partial Purification of *Quinoa* Leachate

The following Example describes an optional column purification step which optimizes phytoecdysteroid and polyphenol content in a *quinoa* leachate (QL).

Briefly, ethanol was removed from liquid QL, and the aqueous suspension was acidified with 1% acetic acid. Carbohydrates and other components were eluted with acidified water through a C18 column and discarded (Phenomonex® Strata C18-E, 55 µm, 70A columns were used in our laboratory). Phytoecdsyteroids and polyphenols were then eluted from the column with acidified 70% ethanol. The 70% ethanol fraction was dried to produce dry QL-S (sugar free *quinoa* concentrate), which contained 5% 20HE, 6% total phytoecdysteroids, and 22% total flavonoid glycosides (polyphenols). The column was washed with acidified 95% ethanol to remove *quinoa* oil(s), and prepped with water for re-use. Total recovery of QL and 20HE from the column is high (95.4% and 93.6%, respectively); the 70% ethanolic fraction (QL-S) represents 13.3% of the initial weight QL. See Table 4 below.

TABLE 4

Yield and 20-hydroxyecdysone (20HE) content of three fractions produced through C18 column purification of QL. Data are the mean ± SEM of separately produced QL-S batches (n = 3-7).

| Column Fraction | Yield (% w/w of QL) | 20HE Content (%) |
|---|---|---|
| Water | 71.3 (±0.4) | Not detectable |
| 70% EtOH (QL-S) | 13.3 (±0.4) | 4.90 (±0.09) |
| 95% EtOH | 10.8 (±0.3) | Not detectable |

Biochemical analysis of the QL-S was performed as described in Example 3. Phytochemical content was determined using LC-UV-MS, the results of which are shown below in Table 5.

TABLE 5

Retention time, chemical identification, m/z, and concentration of phytochemicals in a representative batch of partially purified quinoa leachate (QL-S)

| Peak No. | UV $R_t$ (min) | Compound | $[M + H]^+$ | $[M - H]^-$ | Fragment m/z | Conc. (mg/g) |
|---|---|---|---|---|---|---|
| 1 | 24.13 | Quercetin trisaccharide I | 757 | 755 | 611, 303 | 85.2 |
| 2 | 25.51 | Quercetin glycoside I | — | — | 303 | 6.0 |
| 3 | 27.49 | Quercetin trisaccharide II | 743 | 741 | 611, 465, 303 | 46.3 |
| 4 | 31.54 | Quercetin trisaccharide III | 743 | 741 | 611, 303 | 5.0 |
| 5 | 37.86 | Kaempferol trisaccharide | 741 | 739 | 595, 449, 287 | 47.4 |
| 6 | 40.59 | Quercetin glycoside II | — | — | 303 | 11.5 |
| 7 | 45.25 | Quercetin glycoside III | — | — | 303 | 24.5 |
| 8 | 48.52 | 20-Hydroxyecdysone | 481 | 539* | 463 | 51.5 |
| | | TOTAL FLAVONOID GLYCOSIDES | | | | 225.8** |

Rt = retention time
Conc. = concentration
*Indicates the reported $[M - H]-$ represents an acetic acid adduct $[M - H + C_2H_4O_2]-$
**Total polyphenols were estimated as gallic acid equivalents using the Folin-Ciocalteu assay to be 8.6% in QL-S.

Figure 6:
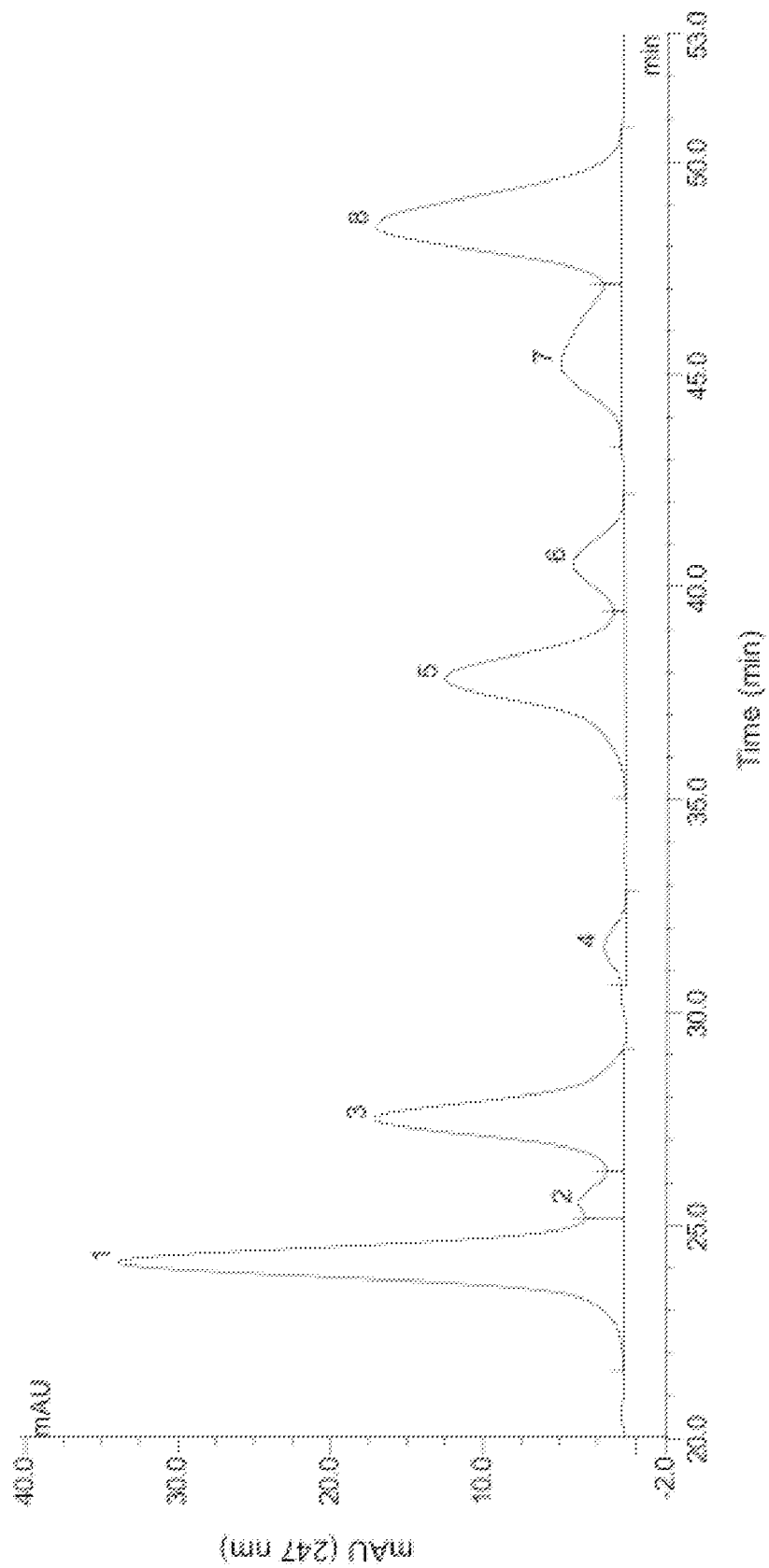
FIG. 6. LC-UV chromatogram (247 nm) of a representative batch of QL-S (1 mg/ml; 1 μl injection) using isocratic 11% acetonitrile. Peaks correspond with those in Table 5. LC-UV analysis was performed at 247 nm alongside external standard of 20HE and purified quercetin trisaccharide I using a C8 column with isocratic 11% ACN over 60 min. Compounds were putatively identified by UV retention time, MS m/z and fragmentation pattern, and those reported in literature.

FIG. 6 shows the molecular structures and LC-UV chromatogram at 247 nm of QL-S (1 mg/ml; 1 µl injection) phytochemical components. Eight peaks corresponding with eight different molecules were identified as listed above in Table 5, including 3 quercetin glycosides, 3 quercetin trisaccharides, 1 kaempferol trisaccharide, and 20-HE.

Concentration of minor phytoecdysteroids present in a representative batch of QL-S was also determined. Briefly, LC-UV analysis was performed at 247 nm alongside external standard of 20HE using a C8 column with a gradient of 7 to 27% ACN over 40 min. Compounds were putatively identified by UV retention time, MS m/z and fragmentation pattern, and those reported in literature.

TABLE 3

Concentration of minor phytoecdysteroids present in a representative batch of QL-S.

| Minor Phytoecdsyteroid | Conc. (mg/g) |
|---|---|
| Makisterone A | 4.2 |
| 24-Epi-makisterone A | 3.5 |
| 24(28)-Dehydromakisterone A | 4.3 |
| Ecdysteroid | 1.1 |
| Makisterone C | 1.2 |
| TOTAL PHYTOECDYSTEROIDS | 65.8 |

In summary, the simple column purification step described in this Example provides a *quinoa* concentrate comprising high amounts of phytoecdysteroid and polyphenol compounds in the absence of carbohydrates or oils.

Numerous modifications and variations in the practice of the invention are expected to occur to those of skill in the art upon consideration of the presently preferred embodiments thereof. Consequently, the only limitations which should be placed upon the scope of the invention are those which appear in the appended claims.

All of the U.S. patents, U.S. patent application publications, U.S. patent applications, foreign patents, foreign patent applications and non-patent publications referred to in this specification and/or listed in the Application Data Sheet, are incorporated herein by reference, in their entireties or in relevant part, as would be apparent from the context of their citation.

From the foregoing it will be appreciated that, although specific embodiments of the disclosure have been described herein for purposes of illustration, various modifications may be made without departing from the spirit and scope of the full disclosure.

REFERENCES

1. Vega-Galvez et al. (2010) Nutrition facts and functional potential of *quinoa* (*Chenopodium quinoa* Willd.). an ancient Andean grain: a review. J Sci Food Agric 90: 2541-2547.
2. FAO (2011) *Quinoa*: an ancient crop to contribute to world food security. pp. 1-55.
3. Hellin J, Higman S (2003) *Quinoa* and food security. In: Hellin J, Higman S, editors. Feeding the market: South American farmers, trade and globalization. Bloomfield, C T: Kumarian Press, Inc. pp. 89-114.
4. Abugoch James L E (2009) *Quinoa* (*Chenopodium quinoa* Willd.): composition, chemistry, nutritional and functional properties. Adv Food Nutr Res 58: 1-31.
5. FAO (2012) Master plan for the international year of *quinoa*: a future sown thousands of years ago. pp. 1-26.
6. Kumpun S, Maria A, Crouzet S, Evrard-Todeschi N, Girault J-P, et al. (2011) Ecdysteroids from *Chenopodium quinoa* Willd., an ancient Andean crop of high nutritional value. Food Chem 125: 1226-1234.
7. Zhu N, Kikuzaki H, Vastano B C, Nakatani N, Karwe M V, et al. (2001) Ecdysteroids of *quinoa* seeds (*Chenopodium quinoa* Willd.). J Agric Food Chem 49: 2576-2578.
8. Dinan L (2009) The Karlson Lecture. Phytoecdysteroids: what use are they? Arch Insect Biochem Physiol 72: 126-141.
9. Rharrabe K, Sayan F, Lafont R (2010) Dietary effects of four phytoecdysteroids on growth and development of the Indian meal moth, *Plodia interpunctella*. J Insect Sci 10: 1-12.
10. Arnault C, Slama K (1986) Dietary effects of phytoecdysones in the leek-moth, *Acrolepiopsis assectella* Zell. (Lepidoptera: Acrolepiidae). J Chem Ecol 12: 1979-1986.
11. Blackford M J P, Dinan L (1997) The effects of ingested 20-hydroxyecdysone on the larvae of *Aglais urticae, Inachis io, Cynthia cardui* (Lepidoptera, Nymphalidae) and *Tyria jacobaeae* (Lepidoptera, Arctiidae). J Insect Physiol 43: 315-327.
12. Singh P, Russell G B (1980) The dietary effects of 20-hydroxyecdysone on the development of housefly. J Insect Physiol 26: 139-142.
13. Marion-Poll F, Descoins C (2002) Taste detection of phytoecdysteroids in larvae of *Bombyx mori, Spodoptera littoralis* and *Ostrinia nubilalis*. J Insect Physiol 48: 467-476.
14. Slama K, Lafont R (1995) Insect hormones—ecdysteroids: their presence and actions in vertebrates. Eur J Entomol 92: 355-377.
15. Gorelick-Feldman et al. (2008) Phytoecdysteroids increase protein synthesis in skeletal muscle cells. J Agric Food Chem 56: 3532-3537.
16. Seidlova-Wuttke D et al. (2010) Beta-ecdysone has bone protective but no estrogenic effects in ovariectomized rats. Phytomedicine 17: 884-889.
17. Kapur et al. (2010) Beneficial effects of beta-edysone on the joint, epiphyseal cartilage tissue and trabecular bone in ovariectomized rats. Phytomedicine 17: 350-355.
18. Syrov V N, Khushbaktova Z A (1996) Wound-healing effects of ecdysteroids. Doklady Akademii Nauk Respubliki Uzbekistana 12: 47-50.
19. Kokoska L, Janovska D (2009) Chemistry and pharmacology of *Rhaponticum carthamoides*: a review. Phytochemistry 70: 842-855.
20. Lafont R (1998) Phytoecdysteroids in world flora: diversity, distribution, biosynthesis and evolution. Russ J Plant Physiol 45: 276-295.
21. Bathori M (2002) Phytoecdysteroids effects on mammalians, isolation and analysis. Mini Rev Med Chem 2: 285-293.
22. Kizelsztein P, Govorko D, Komarnytsky S, Evans A, Wang Z, et al. (2009) 20-Hydroxyecdysone decreases weight and hyperglycemia in a diet-induced obesity mice model. Am J Physiol Endocrinol Metab 296: E433-439.
23. Foucault et al. (2011) *Quinoa* extract enriched in 20-hydroxyecdysone protects mice from diet-induced obesity and modulates adipokines expression. Obesity 20: 270-277.
24. Graf B L et al. (2010) Plant-derived therapeutics for the treatment of metabolic syndrome. Curr Opin Investig Drugs 11: 1107-1115.
25. O'Day M et al. (1998) Corn Insect Pests: A Diagnostic Guide. Missouri Manual 166, Illinois Manual C1358. Columbia, Miss.: M U Extension, University of Missouri. 49 p.
26. Bakrim et al. (2008) Ecdysteroids in spinach (*Spinacia oleracea* L.): biosynthesis, transport and regulation of levels. Plant physiology and biochemistry: PPB/Societe francaise de physiologie vegetale 46: 844-854.
27. Dinan L, Whiting P, Scott A J (1998) Taxonomic disribution of phytoecdysteroids in seeds of members of the chenopodiaceae. Biochem Syst Ecol 26: 553-576.

28. Roopchand D E et al. (2012) Biochemical analysis and in vivo hypoglycemic activity of a grape polyphenol-soybean flour complex. J Agric Food Chem 60: 8860-8865.
29. Roopchand et al. (2012) Efficient sorption of polyphenols to soybean flour enables natural fortification of foods. Food Chem 131: 1193-1200.
30. Cheng et al. (2012) In vivo and in vitro antidiabetic effects of aqueous cinnamon extract and cinnamon polyphenol-enhanced food matrix. Food Chem 135: 2994-3002.
31. Grace et al. (2009) Hypoglycemic activity of a novel anthocyanin-rich formulation from lowbush blueberry, *Vaccinium angustifolium* Aiton. Phytomedicine 16: 406-415.
32. Rojo et al. (2012) In vitro and in vivo anti-diabetic effects of anthocyanins from maqui berry (*Aristotelia chilensis*). Food Chem 131: 387-396.
33. Ribnicky et al. (2009) Improved absorption and bioactivity of active compounds from an anti-diabetic extract of *Artemisia dracunculus* L. Int J Pharm 370: 87-92.
34. Kellogg et al. (2010) Alaskan wild berry resources and human health under the cloud of climate change. J Agric Food Chem 58: 3884-3900.
35. Jeong S M, Kang M J, Choi H N, Kim J H, Kim J I (2012) Quercetin ameliorates hyperglycemia and dyslipidemia and improves antioxidant status in type 2 diabetic db/db mice. Nutr Res Pract 6: 201-207.
36. Kelly G S (2011) Quercetin: monograph. Altern Med Rev 16: 172-194.
37. Saragusti et al. (2010) Inhibitory effect of quercetin on matrix metalloproteinase 9 activity: molecular mechanism and structure-activity relationship of the flavonoid-enzyme intereaction. Eur J Dermatol 644: 138-145.
38. Da-Silva et al. (2007) The small polyphenolic molecule kaempferol increases cellular energy expenditure and thyroid hormone activation. Diabetes 56: 767-776.
39. Zhang et al. (2007) Increasing dietary leucine intake reduces diet-induced obesity and improves glucose and cholesterol metabolism in mice via multimechanisms. Diabetes 56: 1647-1654.
40. Kuljanabhagavad T, Wink M (2009) Biological activities and chemistry of saponins from *Chenopodium quinoa* Willd. Phytochem Rev 8: 473-490.
41. Shi et al. (2004) Saponins from edible legumes: chemistry, processing, and health benefits. J Med Food 7: 67-78.

What is claimed is:

1. A method of producing a leachate comprising 20-hydroxyecdysone from an intact *quinoa* seed comprising:
    contacting the intact quinoa seed with a leaching fluid to produce a leaching mixture comprising the 20-hydroxyecdysone, wherein the leaching fluid is selected from the group consisting of water, n-butanol, isopropanol, n-propanol, aqueous ethanol having a concentration less than 95% ethanol, methanol, ethyl acetate, nitromethane and formic acid, and wherein the contacting step is performed at a temperature of less than 80° C.; and
    separating the quinoa seed from the leaching mixture, thereby producing a leachate comprising 20-hydroxyecdysone from the *quinoa* seed, wherein the leachate comprises from about 100 µg to about 400 µg 20-hydroxyecdysone per gram of seed.

2. The method of claim 1, wherein the *quinoa* seed is a *Chenopodium quinoa* plant seed.

3. The method of claim 1, wherein the leaching fluid comprises 60-80% ethanol.

4. The method of claim 3, wherein the leaching fluid comprises 70% ethanol.

5. The method of claim 1, wherein the contacting step is performed at room temperature.

6. The method of claim 1, wherein the separating step is performed using a method selected from the group consisting of filtration, sedimentation, centrifugation, evaporation, reduced-pressure distillation, precipitation, lyophilization and adsorption.

7. The method of claim 1, further comprising drying the leachate.

8. The method of claim 7, wherein the drying is performed by using a method selected from the group consisting of air drying, spray drying, speed vacuum, rotoevaporation, and lyophilization.

* * * * *